| United States Patent [19] | | [11] | 4,063,952 |
|---|---|---|---|
| Himmelmann et al. | | [45] | Dec. 20, 1977 |

[54] PROCESS FOR HARDENING SILVER HALIDE CONTAINING PHOTOGRAPHIC LAYERS WITH SULPHO- OR SULPHOALKYL-SUBSTITUTED CARBAMOYL PYRIDINIUM COMPOUNDS

[75] Inventors: Wolfgang Himmelmann, Opladen; Johannes Sobek; Wolfgang Sauerteig, both of Leverkusen, all of Germany

[73] Assignee: AGFA-Gevaert Aktiengesellschaft, Leverkusen, Germany

[21] Appl. No.: 604,010

[22] Filed: Aug. 12, 1975

[30] Foreign Application Priority Data

Aug. 17, 1974 Germany ............................ 2439551

[51] Int. Cl.² ............................................... G03C 1/30
[52] U.S. Cl. ........................................ 96/111; 96/67; 96/77; 96/50 PT; 260/112 R; 260/117; 427/338; 106/125
[58] Field of Search ............... 96/111, 67, 77, 50 PT; 260/117, 112; 106/125; 427/338

[56] References Cited

U.S. PATENT DOCUMENTS

| 3,645,743 | 2/1972 | Mucke et al. ........................ 96/111 |
| 3,676,143 | 7/1972 | Himmelmann et al. .............. 96/111 |
| 3,880,665 | 4/1975 | Himmelmann ....................... 96/111 |

*Primary Examiner*—Won H. Louie, Jr.
*Attorney, Agent, or Firm*—Connolly and Hutz

[57] ABSTRACT

In a process for hardening photographic protein containing layers as quick acting hardener a carbamoyl pyridinium compound is used the pyridine ring of which carries a sulfoalkyl substituent.

9 Claims, No Drawings

PROCESS FOR HARDENING SILVER HALIDE CONTAINING PHOTOGRAPHIC LAYERS WITH SULPHO- OR SULPHOALKYL-SUBSTITUTED CARBAMOYL PYRIDINIUM COMPOUNDS

This invention relates to a process for hardening photographic layers which contain protein, in particular gelatine.

Several substances have been described as hardeners for proteins, and in particular gelatine. They include, for example, metal salts such as chromium, aluminum or zirconium salts; aldehydes and halogenated aldehyde compounds, in particular formaldehyde, dialdehydes and mucochloric acid; 1,2- and 1,4-diketones such as cyclohexane-1,2-dione and quinones as well as chlorides of dibasic organic acids; anhydrides of tetracarboxylic acids; compounds which contain several reactive vinyl groups such as vinyl sulphones; acrylamides; compounds containing at least two heterocyclic three-membered rings which can easily be split off, such as ethylene oxide and ethylene imine; polyfunctional methane sulphonic acid esters and bis-α-chloracyl amido compounds. High molecular weight hardeners such as polyacrolein and its derivatives or copolymers and alginic acid derivatives have recently become known. These are used mainly as hardeners which are confined to their layer.

The use of the above mentioned compounds for photographic purposes has, however, several serious disadvantages. Some of these compounds are photographically active and therefore unsuitable for hardening photographic materials while others have such a harmful effect on the physical properties of gelatine layers, for example their fragility, that they cannot be used. Others again bring about discoloration or a change in pH during the hardening reaction. Furthermore, it is particularly important for hardening photographic layers that hardening should reach its maximum as soon as possible after drying begins, so that the material which is required to be hardened does not continuously alter its permeability to the developer solution as is the case with mucochloric acid or formaldehyde, for example.

Certain cross-linking agents for gelatine also have a damaging effect on the skin, for example the ethyleneimine compounds, and they are therefore unsuitable on physiological grounds.

It is also known to use trichlorotriazine, hydroxydichlorotriazine and dichloroaminotriazines as hardeners. The disadvantage of these hardeners is their relatively high vapour pressure, the liberation of hydrochloric acid during hardening and the physiological action of these compounds. Water-soluble derivatives which contain carboxyl and sulphonic acid groups and which are obtained by the reaction of cyanuric chloride with 1 mol of diaminoalkyl or diaminoarylsulphonc acid or carboxylic acid do not have these disadvantages and have therefore recently been proposed as hardeners. Their practical utility is, however, limited by the fact that owing to their high solubility they decompose when left to stand in aqueous solution and therefore rapidly lose their activity.

Finally, when choosing a hardener for photographic layers which contain gelatine, it is of major importance both from the point of view of preparing the material and from the point of view of processing it that the onset of the cross-linking reaction should also be controllable to a certain extent, for example by choice of the drying temperature or choice of pH.

Compounds which contain two or more acrylic acid amido or vinyl sulphone groups in the molecule are also known as hardeners for photographic gelatine layers, for example divinylsulphone, arylene-bis-vinylsulphones, N,N',N''-tris-acryloyl-hydrotriazine and methylene-bis-sulphonamide.

Although the compounds achieve sufficient hardening after some time, they are so sparingly soluble in water that hardening is liable to be uneven within the layer.

The consequences of the undesirable properties of known hardeners described above are extremely important from a photographic point of view, since important photographic properties such as the gradation and sensitivity and, in many cases, also the silver covering power, depend on the degree of cross-linking of the layer-forming colloid and alter during storage. This defect can be attenuated but not completely eliminated, by briefly after-treating the solidified layer with ammonia or an amine. There is the added consideration that aliphatic divinyl sulphones have properties which are damaging to the skin.

A group of hardeners for photographic protein-containing layers which is particularly interesting in this connection has been disclosed in German Offenlegungsschrift No. 2,225,230. These hardeners are carbamoylammonium compounds in which the quaternary nitrogen atom is a member of a 5 or 6-membered heterocyclic ring. The compounds belong to the group of quick-acting hardeners with which photographic materials can be hardened to an optimum degree within a very short time. Some of these compounds, however, in particular those derived from unsubstituted pyridine or from pyridine substituted with lower alkyl groups, have a pronounced odour which restricts their photographic use. Other compounds of this group, which do not present any problem with regard to their odour, give rise to pyridine derivatives during the hardening reaction, which have a harmful effect on the photographic properties of the hardened materials. They are liable to fog the material as well as to alter its sensitivity and they may diminish the development of the magenta layers in colour photographic materials.

It is an object of this invention to provide quick acting hardeners which can harden photographic layers which contain protein without producing an unpleasant odour or having a deleterious effect on the photographic properties.

A process for hardening photographic layers which contain protein, in particular gelatine, has now been found which is characterised by the use of a carbamoyl pyridinium compound in which the pyridine ring carries a sulpho or sulphoalkyl substituent.

The hardeners of the present invention have the general formula

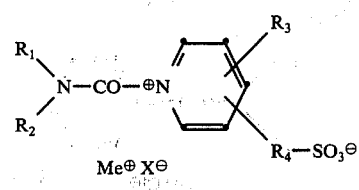

in which $R_1$ and $R_2$ may be the same or different and represents alkyl group containing 1 to 3 carbon atoms, an aryl group which may be substituted with a lower alkyl group or with halogen, for example phenyl which may be substituted with methyl, ethyl, chlorine or bromine; an aralkyl group, e.g. benzyl, which may be substituted in the same way as the aryl group, or $R_1$ and $R_2$ together form the atoms required to complete a piperidine or morpholine ring, which ring may be substituted with alkyl such as methyl or ethyl or with halogen such as chlorine or bromine.

$R_3$ represents hydrogen, methyl or ethyl, $R_4$ represents methylene, ethylene, propylene or a single chemical bond, $Me^+$ represents an alkali metal cation such as $Li^+$, $Na^+$ or $K^+$ and $X^-$ represents an anion such as $Cl'$ or $Br'$.

The following compounds are given as examples of hardeners corresponding to the above general formula:

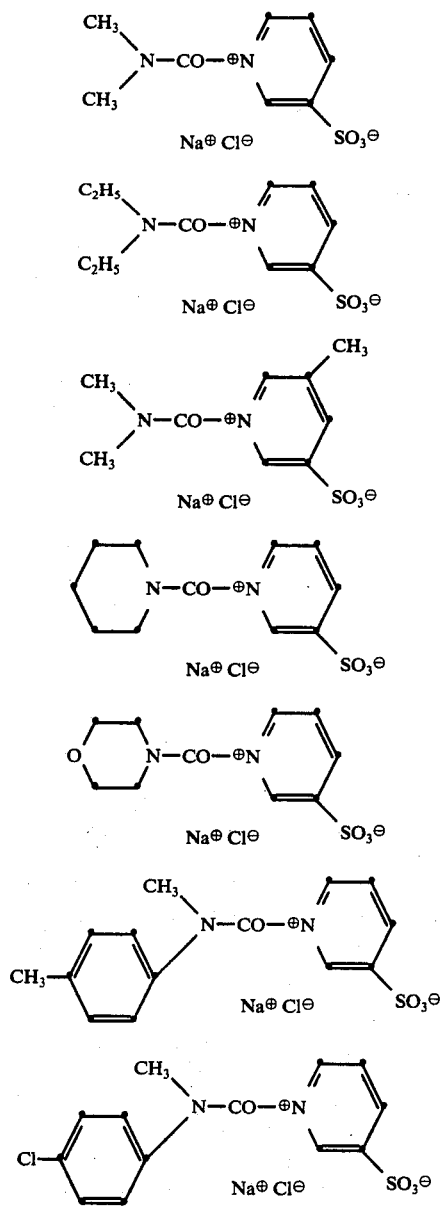

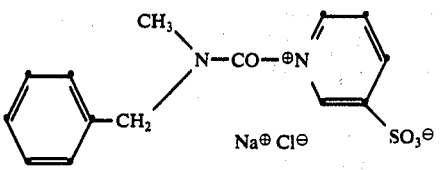

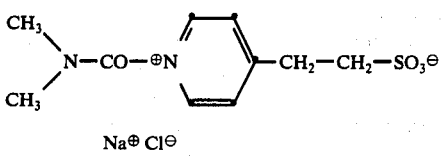

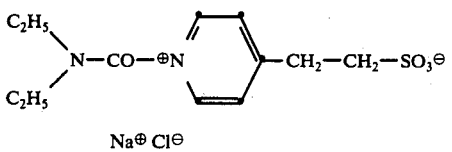

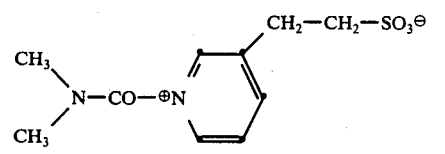

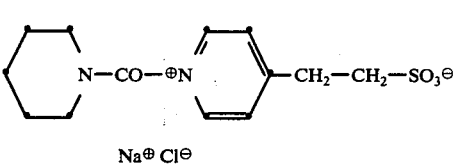

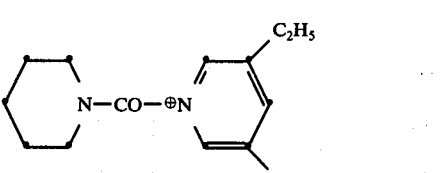

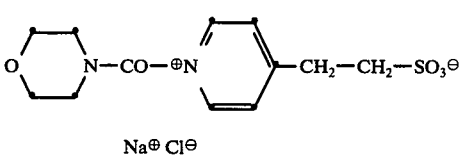

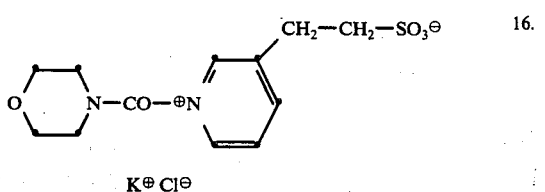

-continued

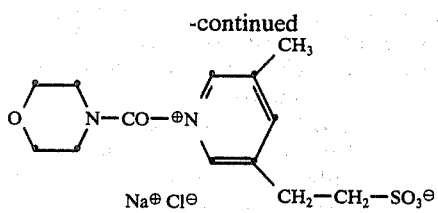

17.

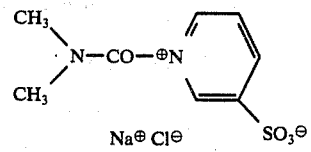

The compounds can be prepared by simple methods which are generally known from the literature. Reference may be made in this connection of Chem. Ber. 40, 1907, page 1831 and J. Phys. Chem. 68 3149 (1964). The carbamic acid chlorides are prepared from the secondary amines, for example by reaction with phosgene, and they in turn are reacted with pyridine compounds which are not steam distillable. The reaction is carried out with the exclusion of light. The method of preparation is described below the reference to compound 5 used as example:

A. Preparation of morpholine carbonyl chloride

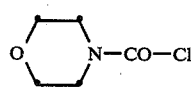

49.5. g of phosgene were slowly introduced into
400 ml of absolute toluene. A solution of
87 g of distilled morpholine in
450 ml of absolute toluene was then introduced dropwise into this mixture at room temperature with vigorous stirring.

The mixture was then heated to 80° to 90° C for 30 minutes and cooled and the precipitated hydrochloride was suction filtered. The precipitate was washed with absolute toluene. The filtrate was evaporated off under vacuum with exclusion of moisture. An oil was left behind, which was subsequently distilled.

The b.p.$_{1\ mm}$ was 72° C and the yield was 50 g.

B. Preparation of compound 5

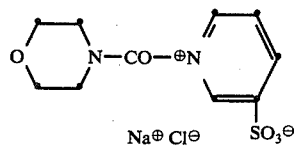

15.9 g of Pyridinesulphonic acid-(3) were dissolved in 200 ml of absolute dimethylformamide. A solution of 2.6 g of sodium in 150 ml of absolute methanol was added dropwise (at pH 7).

The resulting solution was filtered to remove a small quantity of insoluble residues and then reacted with 18.9 g of morpholinyl carbonyl chloride. The mixture was left to stand at room temperature for 24 hours. The reaction product had by that time partly precipitated. The yield was improved by the addition of absolute ether.

The residue was suction filtered and washed with absolute ether.

The yield was 18 g and the melting point was 236° to 237° C.

The other compounds were prepared in a similar manner.

Preparation of compound 1:

15.9 g of Pyridine sulphonic acid-(3) were suspended in 200 ml of absolute dimethylformamide. A solution of 2.6 g of sodium in 150 ml of methanol (pH 7) was added dropwise. The resulting solution was filtered and 13 g of N,N- dimethylcarbamic acid chloride were added. The mixture was left to stand overnight at room temperature. The reaction product was precipitated by the addition of 400 ml of ether. It was suction filtered and thoroughly washed with ether.

The yield was 19.5 g and the decomposition point was 250° C.

Preparation of compound 4:

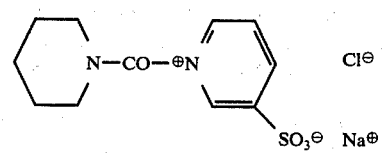

18 g of the sodium salt of pyridine-3-sulphonic acid were dissolved in a mixture of 100 ml of dimethylformamide (anhydrous) and 100 ml of methanol, and 15 g of piperidinocarbonyl chloride were added. The mixture was left to stand overnight and the reaction product was then precipitated with 200 ml of ether. It was suction filtered and rewashed with ether.

The yield was 13 g and the decomposition point was above 250° C.

Preparation of compound 6:

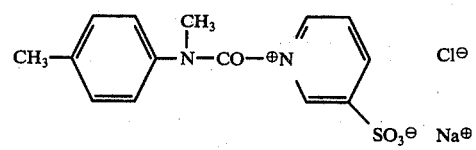

18.2 g of the sodium salt of pyridine-3-sulphonic acid were dissolved in a mixture of 100 ml of methanol and 100 ml of dimethylformamide. 18.5 g of N-methyl-N-methylphenylcarbonyl chloride were added to the mixture. A few crystals precipitate after the mixture had been left to stand for 3 days. They were suction filtered and washed with ether.

The yield was 3 g and the melting point was above 300° C.

Preparation of compound 15:

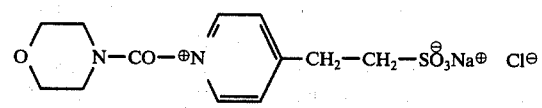

18.9 g of the sodium salt of pyridine-4-ethanesulphonic acid were dissolved in a solution of 400 ml of dimethylformamide (anhydrous) and 400 ml of methanol (anhydrous). 15 g of morpholinylcarbonyl chloride were added. The mixture was left to stand overnight and the reaction product was then precipitated with 1.3

1 of ether. The crystals were suction filtered and washed with ether.

The yield was 22 g and the melting point was 152° to 153° C.

|   | Analysis: | |
|---|---|---|
|   | Calculated: | Found: |
| C | 40.1 % | 39.6 % |
| H | 4.5 % | 4.7 % |
| Cl | 9.9 % | 10.1 % |
| N | 7.8 % | 7.2 % |
| S | 8.9 % | 9.3 % |
| Na | 6.4 % | 6.2 % |

The odour threshold of pyridine is 0.0004 mg/m$^3$ of air, which means that pyridine can be detected by the olfactory sense in very small quantities. The maximum workplace concentration of pyridine, on the other hand, is substantially higher, namely 15 mg/m$^3$. The odour test is therefore a perfectly suitable method for establishing the presence of very small quantities of pyridine concentration at the workplace. The workplace concentration of pyridine should not exceed the limiting value of 15 mg/m$^3$ of air (Reichhard, Lesungsmitteleffekte in der organischen Chemie, Verlag Chemie, page 172).

The compounds used as hardeners according to the present invention are odourless since they are fixed in the layer. This can easily be demonstrated by evaporating about 1 ml of a 5% aqueous solution of a compound to dryness and testing the process by smell to detect any pyridine-like odour. The compound is subjected to similar conditions when it is used for hardening, for example for hardening photographic layers according to the present process. The fact that the carbamoylonium compounds which contain sulphonic acid groups described above are found to be practically odourless under the given conditions also means that they can be processed without any risk of the maximum workplace concentration being exceeded.

Another major advantage compared with the carbamoylonium compounds hitherto known arises from the fact that the latter decompose into basic pyridine derivatives which have a deleterious effect on the photographic properties. They cause a tendency to fogging and changes in sensitivity after storage in a heating cupboard and under tropical conditions and, in the case of colour photographic materials they result in a reduction in the final density of the magenta layers. The compounds according to the invention, by contrast, decompose into betaine type compounds which contain sulpho groups; these compounds are much more photographically inert.

The compounds used according to the invention are advantageously added to the photographic layers which are to be hardened immediately before they are cast, preferably in the form of aqueous or alcoholic solutions. This method of addition immediately before casting is necessary because the compounds react very rapidly with gelatine or any of the other proteins commonly used in photography. Once the compounds have been added, the solutions should be cast within a few minutes. The velocity of the hardening reaction depends primarily on the concentration of proteins in the casting solution.

In contrast to derivatives of unsubstituted pyridine or of pyridine which is substituted with lower alkyl groups, which develop a very strong and unpleasant odour when cast and while drying, the compounds according to the invention are able to cross-link gelatine without liberating any gaseous products.

The MAK values (also known as threshold limit values in USA) represent the maximum workplace concentration of a substance in the form of a gas, vapour or dust which can be tolerated in the atmosphere of a workroom in an 8-hour working day over a period of years without damaging the health of the operators in the workroom.

Another possible method of employing the compounds consists of first casting the unhardened casting solutions and then coating the resulting layers with a solution of the hardening compounds. Alternatively, the compounds can be incorporated in the unhardened or only slightly hardened photographic layers by bathing the layers in aqueous solutions containing the compounds and sodium sulphate during the photographic process, for example before development.

By photographic layers are meant in this context any layers used in photographic materials in general, for example light-sensitive silver halide emulsion layers, protective layers, filter layers, antihalation layers, back coating layers or any photographic auxiliary layers in general.

The light-sensitive emulsion layers for which the hardening process according to the invention is particularly suitable include, for example, those layers which are based on unsensitized emulsions, orthochromatic, panchromatic or infra-red emulsions, X-ray emulsions and other spectrally sensitized emulsions. The hardening process according to the invention has also been found suitable for hardening the gelatine layers used for various black and white and colour photographic processes. The process according to the invention has been found particularly advantageous for hardening photographic layer combinations which are used for carrying out colour photographic processes, for example, those which contain emulsion layers with colour couplers or emulsion layers which are intended to be treated with solutions containing colour couplers.

The effect of the compounds used according to the invention is not impaired by the usual photographic additives. The hardeners are also inert towards photographically active substances such as water-soluble and emulsified water-insoluble colour components, stabilizers, and sensitizers. They have no harmful effect on the light-sensitive silver halide emulsions. Furthermore, the compounds can be combined with any compounds from the classes of hardeners previously known, for example with formalin, mucochloric acid, triacryloformal, bis-vinylsulphones, bis-vinylsulphonamides, dialdehydes or bis-chloroacetamides.

Apart from gelatine, the layers may contain water-soluble high polymer compounds, in particular polyvinyl alcohol, polyacrylic acid sodium and other homopolymers or copolymers which contain carboxyl groups, as well as polyvinylpyrrolidone, polyacrylamide or high molecular weight naturally occurring substances such as dextranes, dextrines, starch ethers, alginic acid or alginic acid derivatives.

The concentrations at which the hardeners according to the invention are required to be used may vary within wide limits and depend mainly on the particular hardening compound used.

Satisfactory results are obtained with quantities of 0.1 to 10% by weight and preferably 0.2 to 6% by weight, based on the dry weight of binder.

As already mentioned above, the hardening reaction between the compound according to the invention and gelatine or proteins sets in at once so that the optimum degree of hardening is achieved more or less simultaneously with drying of the layers after they have been passed or processed.

The activity of the hardening compounds is determined by means of the melting point of the layers, which can be measured as follows: The layer cast on a substrate is half dipped in water which is continuously heated to 100° C. The temperature at which the layer runs off the substrate (formation of streaks) is termed the melting point or melting off point. Pure protein layers or gelatine layers which do not contain hardener in no case show an increase in melting point by this method of measurement. The melting off point under these conditions is 30° to 35° C.

The compounds according to the invention react surprisingly rapidly with proteins and make it possible for protein containing materials to be hardened easily to an optimum degree within a very short time. This unexpected effect of the compound is particularly important for the hardening of photographic materials which contain proteins as binders. The degree of hardening can easily be controlled and the materials can be adjusted to the desired degree of hardening practically while they are being prepared without any necessity for prolonged storage times which entail the uncertainty of uncontrollable after-hardening. Added to this is the photographically inert behaviour of the compounds of the invention, because of which they can advantageously be used for hardening colour photographic materials in which the colour components, particularly the magenta components, are particularly sensitive to hardeners.

The invention will now be explained in more detail with the aid of the following examples.

EXAMPLE 1

1% by weight and 2% by weight of compounds 5 and 15, based on the dry weight of gelatine, were added in the form of an aqueous solution at pH 6.2 to 100 ml of a photographic silver bromide gelatine emulsion which was ready for casting and contained 10% by weight of gelatine and, based on the quantity of gelatine, 25% by weight of an emulsified magenta colour coupler of the following formula:

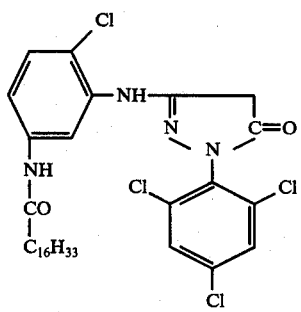

The mixture was stirred vigorously and immediately cast on a prepared cellulose triacetate substrate, using a conventional casting machine, and dried. The usual additives were not altered. After a storage time of 24 hours at room temperature and after exposure behind a graded wedge, the melting off points of the sample layers were determined after colour development:

| Samples | | Layer melting points in ° C | Final density D max of magenta dye |
|---|---|---|---|
| 0 % (without hardening) | | 34 | 2.5 |
| 1 % | Compound 5 | >100 | 2.4 |
| 2 % | | >100 | 2.3 |
| 1 % | Compound 15 | >100 | 2.4 |
| 2 % | | >100 | 2.4 |
| 1 % | Comparison compound $V_1$ | >100 | 1.8 |
| 2 % | | | |
| 1 % | Comparison compound $V_2$ | >100 | 1.9 |
| 2 % | | | |

The compounds used for comparison had the following formulae:

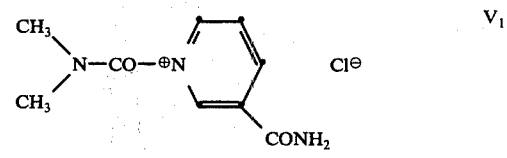

and

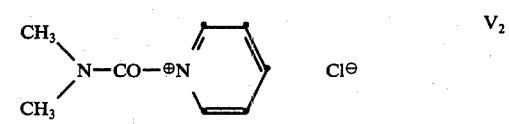

Cross-linking was so vigorous that the layers will not dissolve even in boiling water after 5 minutes. Layers hardened with compound $V_2$ had a strong odour of pyridine which was released by breathing on a sample strip. Layers hardened with compound $V_1$ and those hardened with compounds 5 and 15 were odourless but compound $V_1$ depressed the maximum density of magenta from 2.5 to 1.9. The densities were measured behind a green filter in the usual manner.

The results summarized in the above table clearly indicate the advantageous properties of the compounds according to the invention.

EXAMPLE 2

Sodium sulphate was added to a 5% aqueous solution of compound 1 almost to saturation point. Unhardened photographic colour film samples containing the compound indicated in Example 1 as magenta coupler were dipped in this solution for various lengths of time with exclusion of light. The temperature employed was 22° C. The layers were then briefly rinsed, dried and then stored at room temperature for 12 hours. They were then exposed behind a continuously graded wedge and developed in a colour development process. The activity of these preliminary hardening baths was determined by measuring the layer melting point:

| Immersion time in minutes | Layer melting point in ° C | | Maximum density D max of magenta | |
|---|---|---|---|---|
| | Compound 1 | Compound $V_1$ | Compound 1 | Compound $V_1$ |
| 0.5 | 50° C | 40° C | 2.4 | 2.1 |
| 1 | >100° C | 100° C | 2.2 | 1.9 |

-continued

| Immersion time in minutes | Layer melting point in ° C | | Maximum density D max of magenta | |
|---|---|---|---|---|
| | Compound 1 | Compound V₁ | Compound 1 | Compound V₁ |
| 2 | >100° C | 100° C | 2.2 | 1.8 |
| 3 | >100° C | 100° C | 2.2 | 1.7 |
| untreated layer | 34° C | | 2.4 | |

Determination of the maximum density of magenta was carried out as described in Example 1. At a bath temperature of 40° C, the times required for the compounds to act were much shorter and layer melting points above 100° C were obtained after only 45 seconds. The baths were odourless.

EXAMPLE 3

A 10% casein solution in water was prepared by the addition of sodium hydroxide solution. 0.1 g of tartrazine was added as filter dye to 100 ml of solution. Before the solution was cast, 3% by weight of compounds 1, 4, 5, 10, 12, 13, 15, and 16 dissolved in water were added to various samples of the solution at pH 7. The mixtures were cast on glass plates, and hardened filter foils which are no longer soluble in alkaline water were obtained after drying. None of the compounds had a detectable odour.

EXAMPLE 4

A 20% by weight solution of zein was prepared in a mixture of ethanol and water (8:2) and cast on the back of a cellulose acetate film. The layer obtained after drying could easily be dissolved in a mixture of ethanol and water.

If portions of this film were then bathed for 3 minutes in a solution of
2 g of compound 1, 4, 5, 12 or 15 and
15 g of sodium sulphate in
80 ml of water
and then briefly rinsed and dried in a heating cupboard at 50° to 60° C, the layers were then insoluble in all solvents and effectively cross-linked. The baths were odourless.

EXAMPLE 5

An unhardened silver halide emulsion containing 10% by weight of gelatine as binder and 25% of a pyazolone magenta component as colour coupler as described in Example 1 was cast on a cellulose triacetate substrate without the addition of a hardener. The layer contained all the other usual additives. Samples of the dried layer were then coated with 0.5, 1, 2 and 3% aqueous solutions of compounds 1, 13 and 15 and dried. The compounds were found to be odourless. After exposure in a densitometer and colour development, the melting points of the layers, their swelling values and wet scratch resistances were determined. The results are summarized in the following table.

The swelling values were determined gravimetrically after 10 minutes treatment of the layers in distilled water at 22° C and given in percent.

To determine the wet scratch resistance, a metal tip of a specified size was passed over the wet layer and loaded with increasing weights. The wet scratch resistance is defined by the weight at which the tip leaves a visible scratch trace on the layer. A large weight corresponds to high wet scratch resistance. The colour density of magenta (D max) was determined as described in Example 1.

| Compound | Layer melting point | Swelling in % | Wet scratch resistance in P | Final magenta density (D max) |
|---|---|---|---|---|
| Compound V₁ | | | | |
| 0.5 % | 50° C | 500 | 350 | 1.9 |
| 1 % | | 400 | 450 | 1.8 |
| 2 % | 100° C | 350 | 500 | 1.8 |
| 3 % | | 300 | 550 | 1.5 |
| Compound V₂ | | | | |
| 0.5 % | 60° C | 550 | 320 | 1.9 |
| 1 % | | 450 | 400 | 1.8 |
| 2 % | 100° C | 390 | 450 | 1.7 |
| 3 % | | 340 | 500 | 1.5 |
| Compound 1 | | | | |
| 0.5 % | | 400 | 450 | 2.2 |
| 1 % | 10'100°[1] | 300 | 550 | 2.1 |
| 2 % | | 250 | 600 | 2.1 |
| 3 % | | 200 | 650 | 2.1 |
| Compound 15 | | | | |
| 0.5 % | | 320 | 510 | 2.2 |
| 1 % | | 300 | 650 | 2.1 |
| 2 % | 10'100° | 250 | 700 | 2.1 |
| 3 % | | 250 | 750 | 2.1 |
| unhardened layer | 38° C | 650–800 | — | 2.4 |
| Compound 13 | | | | |
| 0.5 % | | | | |
| 1 % | | 350 | 500 | 2.1 |
| 2 % | 10'100° | 300 | 550 | 2.1 |
| 3 % | | 260 | 600 | 2.0 |
| untreated: | 38° | 600–800 | | 2.4 |

[1] The layer does not dissolve off after 10 minutes in boiling water. The comparison compounds have the formulae indicated in Example 1. Determination of the maximum density of magenta was carried out as described in Example 1.

EXAMPLE 6

To an unhardened silver halide emulsion which contains 10% by weight of gelatine were added 25% by weight, based on the gelatine, of a magenta coupler of the following formula in the form of an emulsion:

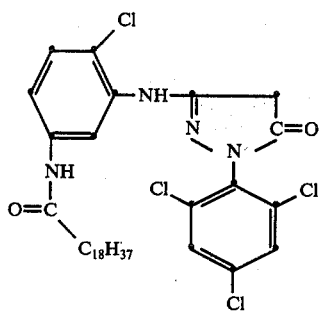

The usual casting additives with the exception of a hardener were then added to the emulsion. The mixture was cast on a prepared polyethylene terephthalate substrate and dried.

Samples of this layer were then covered with aqueous solutions of the compounds (concentrations in each case 1/100 mol per 100 cc of casting solution). After drying and 10 hours' storage, the layers were exceptionally highly cross-linked. The results are recorded in the following table.

The layers were exposed in a densitometer and developed by a colour development process at 22° C.

| Covered with | Layer melting point | Swelling in % | Wet scratch resistance in P | Final magenta density (D max) |
|---|---|---|---|---|
| Compound 15 (1/100 mol per 100 cc of water) | 10'100° C | 310(310)* | 350(350)* | 2.2 |
| Compound 5 (1/100 mol per 100 cc water) | 10'100° C | 260(270)* | 550(550)* | 2.3 |
| Compound 1 (1/100 mol per 100 cc of water) | 10'100° C | 290(290)* | 350(400)* | 2.1 |
| Comparison Compound V₁ (1/1/100 mol per 100 cc of water) | 10'100° C | 290 | 350 | 1.7 |
| Comparison compound V₂ (1/100 mol per 100 cc of water) | 10'100° C | 300 | 390 | 1.8 |
| Covered only with water | 42° C | 800(800) | 50 | 2.4 |

*after 36 hours air conditioning at 56° C and 34% relative humidity

The comparison compounds had the formulae indicated in Example 1. The wet strength was determined as described in Example 5. The magenta density was determined sensitometrically after the samples had been developed in a conventional colour developer, bleached and fixed, the developer containing N,N'-diethyl-p-phenylenediamine as developer substance.

The photographic properties were not affected. The figures given in brackets were measured on materials which had been air conditioned for 36 hours (34% relative humidity, 56° C.). The compounds show no after-hardening.

EXAMPLE 7

A unhardened multilayered colour film consisting of
1. a red sensitive bottom layer 4 μ in thickness, containing, per kg of emulsion, 35 g of silver bromide, 80 g of gelatine and 24 g of 1'-hydroxy-2-[Δ(2,4-di-tert.-amylphenoxy)-n-butyl]-naphthamide,
2. an intermediate layer of gelatine, 2 μ in thickness,
3. a green sensitive middle layer 4 μ in thickness, which contains, per kg of emulsion, 35 g of silver bromide, 80 g of gelatine and 16 g of 1-(2,4,6-trichlorophenyl)-3-[3-α(2,4-di-tert.-amylphenoxy)-acetamidobenzamido]-5-pyrozolone,
4. a 2 μ thick yellow filter layer of colloidal silver in gelatine,
5. a 4 μ thick blue sensitive top layer containing, per kg of emulsion, 35 g of silver bromide, 80 g of gelatine and 20 g of [3[α(2,4-di-tert.-amylphenoxy)acetamido]-benzoyl]-2-methoxy-acetanilide and
6. a 2 μ thick protective layer of gelatine was cast on a 120 μ thick cellulose triacetate substrate in known manner and dried. The film was covered with a 1% aqueous solution of compound 15.

For comparison, two 1% solutions of the following compounds which are not in accordance with the invention were used:

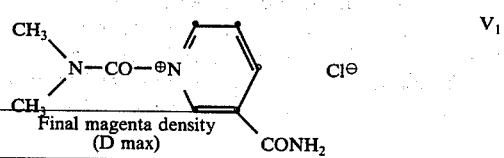

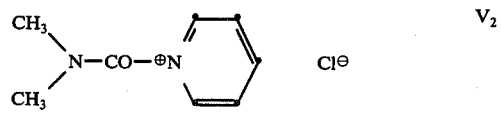

The layer melting points and temperatures at which the layers become detached were determined after drying and after 12 hours' storage at room temperature, and the final colour density of the magenta layer was determined sensitometrically after exposure and colour development as described in Example 6.

| Covered with | Layer detached at | Layer melting point | Final density of magenta layer D max | odour when casting |
|---|---|---|---|---|
| Compound 4 (%) | 100° C | 10'100° C | 2.5 | none |
| V₁ (1%) as comparison V₂ (1%) | 100° C | 10'100° C | 1.5 | none |

| Covered with | Layer detached at | Layer melting point | Final density of magenta layer D max | odour when casting |
|---|---|---|---|---|
| as comparison | 100° C | 10'100° C | 2.3 | strong odour |
| no covering | 40° C | 45° C | 2.5 | none |
| hardened with 1 g/100 g of gelatine of tris-acryloyl hydro-triazine | 12 hours after casting | | | |

The results show that the compound according to the invention hardens very efficiently, produces no odour in the process of casting and drying and does not affect the final density of the magenta layer.

We claim:

1. A process for providing a photographic material comprising at least one silver halide emulsion associated with at least one supported layer containing protein in which the protein-containing layer is contacted with an effective amount of a hardener to harden the layer wherein the improvement comprises the hardener is carbamoylpyridinium compound of the formula

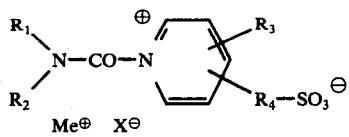

in which $R_1$ and $R_2$ which are the same or different represent an alkyl group containing 1 to 3 carbon atoms, an aryl group which is unsubstituted or substituted which $C_1$ to $C_2$ alkyl or with halogen; or an aralkyl group which is unsubstituted or substituted with $C_1$ to $C_2$ alkyl or with halogen; or $R_1$ and $R_2$ together represent the groups required to complete a piperidine or morpholine ring which is substituted with $C_1$ to $C_2$ alkyl or with halogen, $R_3$ represents hydrogen, methyl or ethyl, $R_4$ represents ethylene or a single chemical bond, Me+ represents an alkali metal cation and X- represents Cl or Br-.

2. Process according to claim 1, characterized by the use of the hardener for hardening layers which contain homopolymers and copolymers which contain carboxyl groups and gelatine as binders.

3. Process according to claim 1, characterized in that the hardener is applied from aqueous solution.

4. Process according to claim 1, characterized in that the hardener is applied from alcoholic solution.

5. Process according to claim 1, characterized in that the hardener is applied from aqueous alcoholic solution.

6. Process according to claim 1, characterized in that the hardener is applied in quantities of 0.2 to 6% by weight, based on the weight of a protein containing binder in a casting solution of the layer which is required to be hardened.

7. Process according to claim 1, characterized in that the layer which is to be hardened is covered with a 0.2 to 10% solution of the hardener and then dried.

8. Process according to claim 1, characterised in that the hardener is applied as a 0.2 to 10% solution before the photographic material is processed.

9. The process according to claim 1 wherein the material is a multilayered color photographic material.

* * * * *

UNITED STATES PATENT AND TRADEMARK OFFICE
CERTIFICATE OF CORRECTION

PATENT NO. : 4,063,952
DATED : DECEMBER 20, 1977
INVENTOR(S) : HIMMELMANN ET AL

It is certified that error appears in the above-identified patent and that said Letters Patent are hereby corrected as shown below:

Title page, left column, line 2 of [75] Inventors:

-- Johannes Sobel --

Column 7, lines 23-24, German word bridging lines 23 and 24 should read as follows: Losungs-mitteleffekte --

Column 12, line 14, "pyazolone" should read -- pyrazolone --

Signed and Sealed this

Ninth Day of May 1978

[SEAL]

Attest:

RUTH C. MASON
Attesting Officer

LUTRELLE F. PARKER
Acting Commissioner of Patents and Trademarks